United States Patent [19]

Stoyan et al.

[11] Patent Number: 5,854,035
[45] Date of Patent: Dec. 29, 1998

[54] ENZYME WITH LEUDH ACTIVITY, NUCLEOTIDE SEQUENCE CODING THEREFOR AND PROCESS FOR THE PREPARTION OF THE ENZYME

[75] Inventors: Tanja Stoyan, Aachen; Maria-Regina Kula, Niederzier, both of Germany

[73] Assignee: Degussa AG, Germany

[21] Appl. No.: 804,699

[22] Filed: Feb. 21, 1997

[30]     Foreign Application Priority Data

Feb. 22, 1996 [DE] Germany ................... 196 06 494.5

[51] Int. Cl.⁶ ............................ C12P 13/06; C12P 13/04; C12N 1/00; C07H 21/04
[52] U.S. Cl. .................. 435/116; 435/106; 435/252.33; 435/320.1; 435/834; 536/23.2
[58] Field of Search ............................ 435/26, 106, 116, 435/189, 191, 252.3, 252.33, 320.1, 834; 536/23.2

[56]         References Cited

PUBLICATIONS

Stoyan et al. (08 Apr. 1996)) Accession U51099, Genbank databases.

Schutte et al. (1985) Applied Microbiol. Biotech. 22, 306–317.

*Primary Examiner*—Robert A. Wax
*Assistant Examiner*—Elizabeth Slobodyarsky
*Attorney, Agent, or Firm*—Cushman Darby & Cushman IP Group of Pillsbury Madison & Sutro LLP

[57]         ABSTRACT

The invention relates to an enzyme with LeuDH activity, to the *B. cereus* nucleotide sequence coding therefor, to the transformation of microorganisms of the genus *E. coli* with a plasmid containing this sequence, and to a process for the preparation of the enzyme.

11 Claims, 2 Drawing Sheets

ENZYME WITH LEUDH ACTIVITY, NUCLEOTIDE SEQUENCE CODING THEREFOR AND PROCESS FOR THE PREPARTION OF THE ENZYME

This application is based on application no. DE 19606494.5 filed in Germany on Feb. 22, 1996, the entire content of which is incorporated hereinto by reference.

BACKGROUND OF THE INVENTION

1. Field of the Invention

The invention relates to an enzyme with LeuDH activity, to the *B. cereus* nucleotide sequence coding therefor, to microorganisms of the genus *E. coli* which contain said sequence, and to a process for the preparation of the enzyme.

2. Background Information

Leucine dehydrogenase (LeuDH, EC 1.4.1.9) is an $NAD^+$-dependent oxidoreductase which catalyzes the reversible deamination of L-leucine and various other aliphatic L-amino acids to their keto analogues, the equilibrium of the reaction lying on the L-leucine side. The enzyme is suitable for the production of L-tert.-leucine and other non-proteinogenous aliphatic amino acids in the enzyme membrane reactor. L-tert.-Leucine functions as a chiral inductor in chemical synthesis and is used in the preparation of drugs, bringing about an improvement in the metabolic stability of peptides and pseudopeptides.

The process for the preparation of L-leucine in a membrane reactor using LeuDH obtained from *B. stearothermophilus* has been described by T. Oshima et al. (1). At 72° C., however, the temperature optimum of LeuDH from *B. stearothermophilus* is more than 10° C. higher than that of LeuDH from *B. cereus*. This species has also been screened as an efficient enzyme producer.

Schütte et al. (2) have described the preparation and purification of the enzyme under discussion. It has a molecular weight of ca. 310 kDa and consists of eight identical subunits of 39 kDa each (3), in contrast to the other known types of LeuDH (the others have 6). LeuDH from *B. cereus* has a temperature optimum of ca. 60° C. and is stable up to 50° C. in the pH range between 5.6 and 9.8 (heat for 30 min in 50 mM potassium phosphate buffer, pH 7.8, containing 0.1% 2-mercaptoethanol). It can be stored in 50% glycerol at −20° C for at least one year without activity loss (2).

These properties make the increased use of LeuDH from *B. cereus* appear advantageous. However, because of toxin formation, *B. cereus* is classified in hazard category 2 (German Law on Epidemics) and may only be handled if increased safety precautions are taken. This makes larger-scale enzyme production from the wild strain unattractive.

SUMMARY OF THE INVENTION

The object of the invention is to provide the enzyme LeuDH known from *B. cereus* by another route. The invention provides a *B. cereus* DNA sequence (DNA fragment) which is characterized in that it codes for an enzyme with leucine dehydrogenase (LeuDH) activity and comprises (a) the nucleotide sequence as set forth in SEQ ID NO:1, or (b) a nucleotide sequence corresponding to the sequence of (a) within the degeneracy of the genetic code, or (c) a nucleotide sequence hybridizing with the sequences of (a) and/or (b).

The mutant of the DNA sequence (a) formed by single or multiple base substitution, removal, insertion or exchange codes for an enzyme with identical biological activity to that of the DNA sequence (a).

The corresponding amino acid sequence between codons 450 and 1550 is set forth in SEQ ID NO:2. The DNA fragment (a) has an overall length of ca. 1.7 kb.

The chromosomal DNA is isolated from the LeuDH-forming microorganism in a manner known per se. This is effected for example by the process of H. Saito and K. Minra, Biochem. Biophys. Acta 72, 619 (1963), or Heinrichs et al. (4). The resulting DNA is then cleaved in a manner known per se for ligation with plasmid DNA. It is preferable to use restriction endonucleases which do not cut the LeuDH gene. The ligation with the plasmid DNA is facilitated by choosing a restriction endonuclease (or restriction endonucleases) for which there is only one cleavage site. The *B. cereus* DNA fragment according to the invention can be inserted by ligation into any plasmids capable of autonomous replication in *E. coli*. Examples which may preferably be mentioned are ColE1, pSC101, pBR322, pACYC177, pCR1 and especially pUC18.

The chromosomal DNA is ligated with the plasmid DNA in a manner known per se, for example by cleavage of the chromosomal donor DNA and the plasmid with the same restriction endonuclease(s) and subsequent ligation of the cleavage products with a DNA ligase (11). It is preferable to choose an SmaI cleavage site and an XbaI cleavage site. With the commercially available pUC18 and the DNA fragment according to the invention, this gives pLeu2 of 4401 bp. This vector has been deposited in the *E. coli* strain XL1 blue under the number DSM 10441 in the German Collection of Microorganisms and Cell Cultures in accordance with the Budapest Convention.

FIG. 1*b* shows the corresponding restriction map. Vector pLeu2 can undergo autonomous replication in *E. coli.*

The vectors carrying the DNA fragment according to the invention can be transformed in a manner known per se to microorganisms of the genus *E. coli*. The enzyme with LeuDH activity is constitutively strongly overexpressed in *E. coli* under the endogenous LeuDH promoter from *B. cereus* and is present in the *E. coli* cells in a proportion of up to ca. 50% of the soluble cell protein. This value exceeds the value found for expression in *B. cereus* by a factor of 10 to 30.

The invention further relates to the use of the vectors containing the DNA fragment according to the invention, in the appropriate transformants, for the preparation of enzymes with LeuDH activity.

The media to be used for incubation of the transformants are synthetic, semisynthetic or natural media such as those in general use. They contain nutrients such as carbon sources, nitrogen sources and inorganic compounds. Examples of favourable carbon sources are sugars such as glucose, fructose or invert sugar, saccharified starch, sorbitol or glycerol. Examples of favourable nitrogen sources are ammonium sulphate, ammonium chloride, ammonium nitrate, ammonium phosphate, ammonium hydroxide, ammonium tartrate, ammonium acetate or urea. Examples of favourable nutrients which can be offered as both nitrogen and carbon sources are peptone, meat extract or corn steep liquor. Examples of favourable inorganic compounds are potassium dihydrogen phosphate, dipotassium hydrogen phosphate, sodium hydrogen phosphate, disodium hydrogen phosphate, magnesium sulphate, magnesium chloride, potassium chloride, sodium chloride, iron(II) sulphate, iron (II) chloride, iron(III) sulphate, iron(III) chloride, manganese sulphate or manganese chloride. Examples of other favourable nutrients are yeast extract or vitamins.

The transformants can be incubated either in a liquid medium or in a solid medium. It is generally advantageous to use a liquid medium. For large-scale production it is particularly advantageous to carry out the incubation with shaking or with aeration and stirring. The incubation temperature is 20° to 45° C., preferably 28° to 37° C. It is advantageous to adjust the medium to a pH of 6 to 9 with a suitable neutralizing agent during the incubation. As a rule the enzyme is present inside the cells.

After expression of the recombinant LeuDH DNA in the chosen E. coli strain, the cells are therefore macerated (e.g. by grinding with glass beads) and the desired enzyme is obtained from the resulting crude extract by methods which are generally known. This crude extract can also be used for the activity test. In this way it is found, in one Example, that the specific LeuDH activity of the enzyme obtained from the recombinant clone according to the invention has increased by a factor of ca. 27 compared with the crude extract similarly obtained from B. cereus (0.6 u/mg→16 u/mg).

The invention also provides the enzyme obtained in this way and its use for the enzymatic synthesis of non-proteinogenous, especially aliphatic L-amino acids by reductive amination of the corresponding α-keto acids.

L-tert.-Leucine is preferably used.

Examples of starting compounds used for the corresponding L-amino acids are 2-oxo-4-methylpentanoic acid (ketoleucine), 2-oxo-3-methylpentanoic acid (ketoisoleucine), 2-oxo-3-methylbutanoic acid (ketovaline), 2-oxopentanoic acid (ketonorvaline), 2-oxo-4-methylhexanoic acid, 2-oxobutanoic acid, 2-oxo-3,3-dimethylbutanoic acid (keto-tert.-leucine), 2-oxohexanoic acid (ketonorleucine), 2-oxo-4,4-dimethylpentanoic acid (ketoneopentylglycine), 2-oxo-3,3-dimethylpentanoic acid, 2-oxo-4-ethylhexanoic acid, 2-oxo-5,5-dimethylhexanoic acid, 2-oxo-3-cyclohexylpropanoic acid and 2-oxo-4,4-dimethylhexanoic acid.

Characteristic features of the enzyme obtained according to the invention are an increased initial activity and a lower product inhibition compared with enzymes known for these purposes from the state of the art.

DETAILED DESCRIPTION OF THE INVENTION

Experimental Section

Figure 1A:
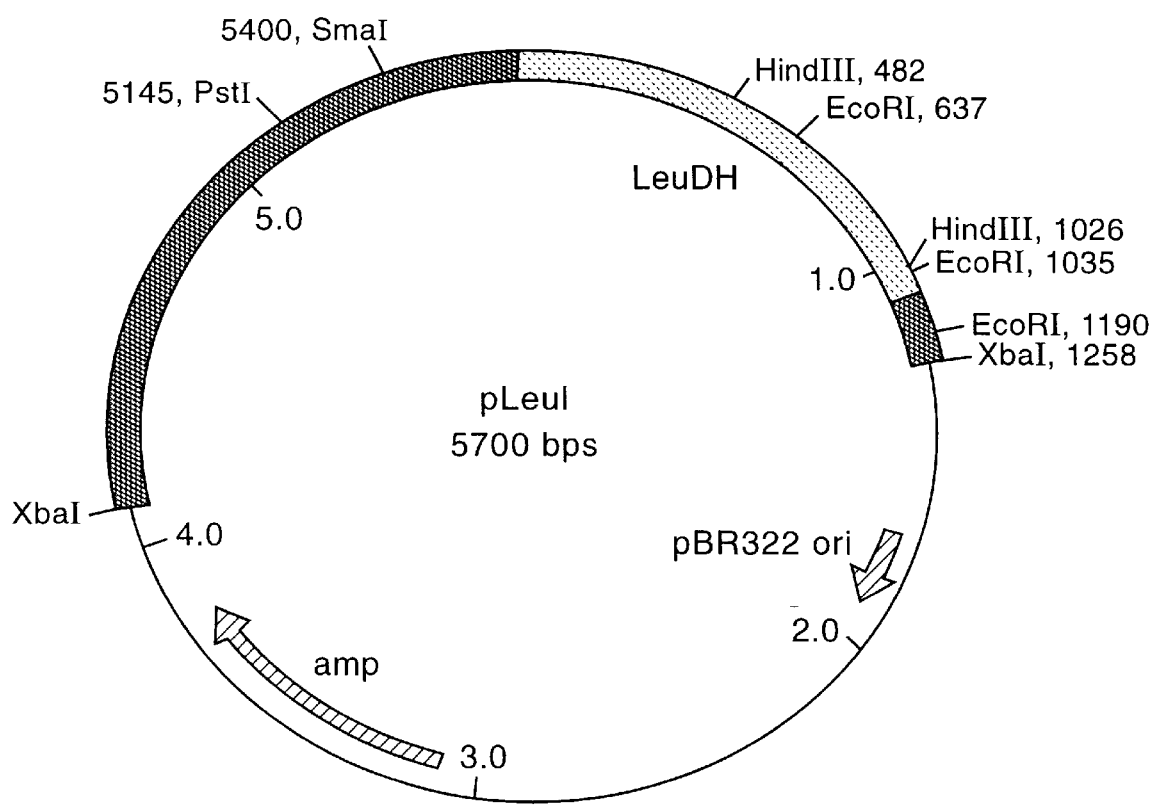
FIG. 1a. Gene for leucine dehydrogenase from *Bacillus cereus* in pUC18.

1. Isolation of Genomic DNA from *B. Cereus*

*B. cereus* DSM 626 was inoculated from the strain collection as an overnight culture in 4 ml of 2% yeast extract, 0.2% $K_2HPO_4$ and 4% glucose and shaken at 30° C. The preculture was used to inoculate 200 ml of the same medium (1:40 dilution) and the cells were left to grow to an $OD_{600}$ of 1.43 (4 h at 30° C.). 1 g of the resulting 2 g of bacterial cells was used for isolation of the genomic DNA. The DNA was isolated essentially by the method of Heinrichs et al. (4). For efficient removal of the DNA, RNAse A (0.1 mg/ml) was added as well as the protease (Quiagen). The yield from 1 g of cells (moist weight) was 1.8 mg of genomic DNA.

2. Preparation of a PCR Fragment of LeuDH

A genome bank was prepared by synthesizing two degenerate primers (TTCGAA/GTATT/CTA/G/TGAAAAATAT/CGATTATGAG/ACAA GGCA/GTTGATCACATAAT-CCGGG/CGCATAGACGAT), which were derived from *B. cereus* protein sequences and the known sequences of already cloned LeuDHs from T. intermedius (5) and *B. stearothermophilus* (6).

The codon usage of B. cereus is shown in Table 1, the information in which can also be found on the Internet under http://tisun4a.lab.nig.ac.jp/codon/cutg.html. With these primers and the genomic DNA as template, an 850 bp DNA fragment could be synthesized in the PCR (100 ng of template, 40 pmol of each primer, 200 μmol of dNTPs, 1.5 mM $MgCl_2$, 2.5 u of Taq polymerase, annealing temperature 42° C., 35 cycles: 1.: denaturation: 5 min at 94° C., 2.-34.: denaturation: 1.30 min at 94° C., annealing: 1.30 min at 42° C., synthesis: 72° C., 35.: last synthesis: 7 min at 72° C.) . The DNA fragment was cloned into vector pUC18 and sequenced according to (7).

3. Detection of the LeuDH Gene by Southern Blotting

To prepare a DIG-labelled DNA probe, the PCR was repeated with the cloned LeuDH fragment as template and the above primers, using DIG-labelled dUTPs (66 μM DIG-11-dUTP, 66 μM dTTP, 134 μM dATP, dCTP, dGTP) (8).

The genomic DNA was cleaved with various restriction enzymes and separated by electrophoresis on a 0.8% agarose gel (50 V, 5 h, RT) and the separated DNA was transferred to a nylon filter and, after UV crosslinking, hybridized with the DNA probe (8). The bound DNA was visualized by chemiluminescence (reagent: CSPD, Luminograph) or by means of a colour reaction (8). The DNA cleaved with the enzyme XbaI showed a band of ca. 3000 bp after hybridization, which was suitable for creating a partial gene bank.

4. Creation of a Partial Gene Bank and Screening With an Activity Test

The genomic DNA separated in the 2000–3000 bp region on the agarose gel was cut out of the gel with the agarose and isolated from the gel with glass milk (Jetsorb). The DNA purified in this way was cloned into vector pUC18 and transformed in Escherichia coli XL1 blue (9). Ca. 500 colonies were picked from this partial genome bank and transferred to master plates. The colonies were transferred to a Whatman filter and subjected to an activity test (6, 10). A clone giving an intense blue colouration was found.

Figure 1B:
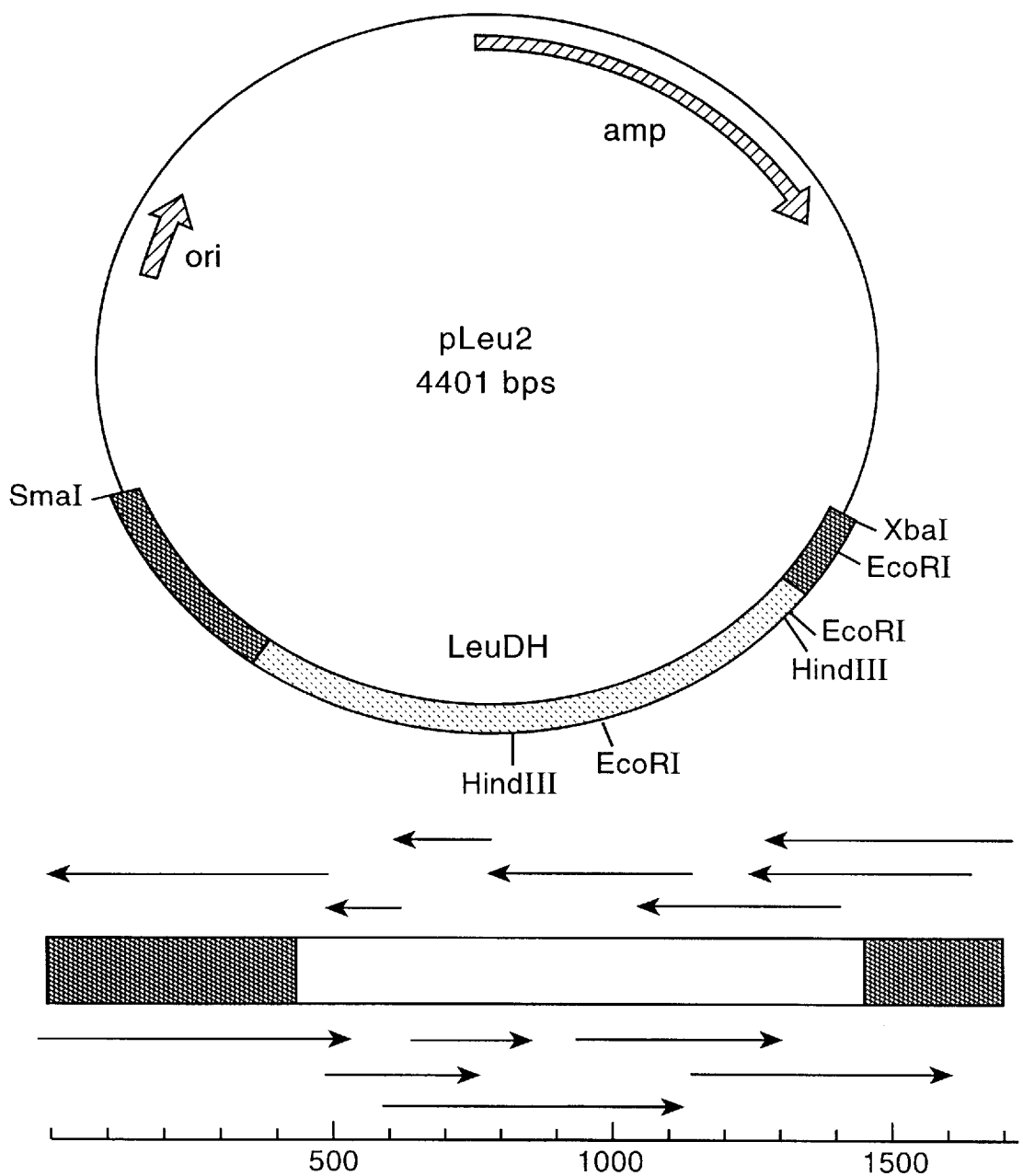
FIG. 1b. Sequencing of the gene for LeuDH from *B. cereus* (pLeu2 with SmaI/XbaI fragment).

5. Characterization of the Recombinant E. Coli Strain 5.1. Determination of the DNA Sequence The plasmid DNA was isolated from the positive E. coli clone and a gene map was created by digestion with various restriction enzymes. The plasmid was called pLeu1 (see plasmid map, FIG. 1a). Plasmid pLeu1 was used to prepare plasmid pLeu2 (FIG. 1b), in which the non-translated region at the 5' end of the gene was shortened to 400 bp by digestion with the restriction enzyme SmaI. Subgenomic fragments were cloned from this plasmid and the complete DNA sequence was determined using the universal and reversal primers from Pharmacia and 5 sequence-specific primers (7). Both strands were sequenced as shown in SEQ ID NO:1. The strain E. coli XL1 blue pLeu2 was deposited under no. DSM 10441 in the German Collection of Microorganisms and Cell Cultures in accordance with the Budapest Convention.

5.2. Expression of the Recombinant LeuDH DNA in *Escherichia Coli*

5.2.1. Activity Test

The recombinant clone was grown overnight in 5 ml of LB medium and the bacteria were centrifuged off, resuspended in 1.6 ml of PBS and then macerated with glass beads (0.3 mm diameter) (2 min in a Vortex). The resulting crude extract was used in an activity test to show an activity of 16 u/mg. The LeuDH activity of the recombinant clone has accordingly been increased by a factor of 30 compared with the crude extract from B. cereus (0.6 u/mg) (2).

5.2.2. Test Procedure 3 ml scale

Solutions required:
  0.1M glycine in 0.1M NaCl solution
  0.1M NaOH
  52.2% of sol. a +47.8% of sol. b gives buffer solution of pH ca. 10.7.
  13.53 mg/ml of KPI, pH 8.0, NAD (20.4 mM)
  8.59 mg/ml of KPI, pH 8.0, L-leucine (65.5 mM)

Assay:
  2000 µl of 0.1M glycine/KCl/KOH buffer, pH 10.7
  500µl of NAD
  500 µl of L-leucine
  25 µl of sample Temp.:
  25° C., λ=340 nm, factor: 19.453

5.3.3. Preparation of LeuDH

The strains were fermented in the following media:

B. cereus (DSM 626):
  2.0% (w/v) of yeast extract
  0.2% (w/v) of $K_2HPO_4$
  4.0% (w/v) of glucose
  pH 7.0
  highest possible oxygenation during the fermentation
  temp.: 30° C.

The growing time at 1% inoculation volume is ca. 6 to 8 h; expected $OD_{562}$ ca. 50; harvest at 1% residual glucose.

E. coli pLeu2:
  LB medium
  0.5% (w/v) of NaCl
  0.5% (w/v) of yeast extract
  1.0% (w/v) of bactotryptone
  100 mg/µl of ampicillin
  pH 7.0 to 8.0
  $PO_2$: 70 to 90%
  temp.: 37° C.

Growing time at 5% inoculation volume ca. 5 h; harvest at $OD_{550}$=3.3.

The following values are obtained:

| Strain | Fermentation volume (1) | Moist weight of bacteria (kg) | Total activity (u) | Volume activity (u/l) | Activity /moist weight (u/kg) |
|---|---|---|---|---|---|
| B. cereus | 200 | 70.7 | 143,000 | 715 | 2023 |
| E. coli pLeu2 | 20 | 0.075 | 8250 | 412 | 110,000 |

LITERATURE

References cited herein are hereby incorporated by reference and are listed below in their entirety for convenience:

1. Oshima et al., Biotechn. Bioeng. Vol XXVII (1985) 1616–1618
2. Schütte et al., Appl. Microbiol. Biotechnol., 22, (1985) 306–317
3. Lünsdorf et al., FEBS Lett., 193(2) (1985) 261–265
4. Heinrichs et al., J. Bacteriol., 175 (1993) 6760–6766
5. Oshima et al., Eur. J. Biochem., 222, (1994), 305–312
6. Nagata et al., Biochemistry, 27 (1988) 9056–9062
7. Sanger et al., Proc. Nat. Acad. Sci. USA, 74 (1977) 5463–5467
8. Boehringer Mannheim, data sheet on "DNA labeling and detection kit: nonradioactive."
9. Bullock et al., BioTechniques, 5 (1987) 376–378
10. Raetz, C.R.H., Proc. Nat. Acad. Sci. USA, 72 (1975) 2274–2278
11. Sambrook, J., Fritsch E. F. and Maniatis, T. (1989) Molecular Cloning. A Laboratory Manual 2nd Ed. Cold Spring Harbor Laboratory Press, Cold Spring Harbor, N.Y.

TABLE 1

Codon usage table

Bacillus cereus [gbbet]: 37 CDS's (10419 codons)
fields: [triplet] [frequency: per thousand] ([number])

| UUU | 25.2( | 263) | UCU | 19.8( | 206) | URU | 32.0( | 333) | UGU | 3.3( | 34) |
|---|---|---|---|---|---|---|---|---|---|---|---|
| UUC | 13.5( | 141) | UCC | 2.1( | 22) | UAC | 10.5( | 709) | UGC | 1.8( | 19) |
| UUA | 43.1( | 449) | UCA | 19.2( | 190) | UAA | 2.6( | 27) | UGA | 0.1( | 1) |
| UUG | 9.2( | 95) | UCG | 2.8( | 29) | UAG | 0.9( | 9) | UGG | 15.8( | 165) |
| CUU | 14.0( | 146) | CCU | 10.6( | 110) | CAU | 16.1( | 168) | CGU | 14.3( | 149) |
| CUG | 1.7( | 18) | CCC | 0.6( | 6) | CAC | 4.2( | 44) | CGC | 4.7( | 49) |
| CUA | 10.3( | 107) | CCA | 17.9( | 196) | CAA | 27.2( | 283) | CGA | 4.7( | 49) |
| CUG | 2.9( | 30) | CCG | 4.5( | 47) | CAG | 6.7( | 79) | CGC | 0.6( | 6) |
| AUU | 41.6( | 433) | ACU | 15.8( | 165) | AAU | 42.8( | 445) | AGU | 13.6( | 142) |
| AUC | 10.6( | 110) | ACC | 1.9( | 20) | AAC | 18.7( | 195) | AGC | 7.0( | 73) |
| AUA | 13.1( | 136) | ACA | 31.3( | 326) | AAA | 60.3( | 628) | ACA | 5.0( | 61) |
| AUG | 22.7( | 237) | ACG | 13.9( | 145) | AAG | 16.9( | 176) | ACG | 2.3( | 24) |
| GUU | 24.1( | 251) | GCU | 25.9( | 270) | GAU | 48.2( | 502) | GGU | 26.7( | 278) |
| GUC | 3.0( | 31) | CGG | 3.3( | 34) | GAC | 9.7( | 101) | GGC | 6.9( | 72) |
| GUA | 33.0( | 344) | GCA | 35.8( | 373) | GAA | 48.0( | 479) | GGA | 31.1( | 324) |
| GUG | 9.4( | 98) | GCG | 12.2( | 127) | CAG | 15.2( | 158) | GGG | 9.7( | 101) |

Coding GC 36.42% 1st letter GC 48.18% 2nd letter GC 36.50% 3rd letter GC 24.75%
Codon usage for each CDS (format)

What is claimed is:

1. A *Bacillus cereus* DNA sequence which codes for an enzyme with leucine dehydrogenase (LeuDH) activity and comprises
   (a) the nucleotide sequence shown in SEQ ID NO:1, or
   (b) a nucleotide sequence corresponding to SEQ ID NO:1 within the degeneracy of the genetic code.

2. A vector capable of autonomous replication in *E. coli*, said vector comprising the DNA sequence according to claim 1.

3. The vector according to claim 2 which is characterized by the restriction map of FIG. 1*b*.

4. The vector according to claim 2, wherein said vector is pLeu2 contained in the strain *E. coli* XL1-blue pLeu2 deposited under Accession No. DSM 10441.

5. A microorganism of the species *E. coli* with a high productivity for LeuDH, said microorganism comprising a vector according to claim 4.

6. A microorganism of the species *E. coli* which is deposited as the strain *E. coli* XL1-blue pLeu2 under Accession No. DSM 10441.

7. A process for the preparation of leucine dehydrogenase (LeuDH), said process comprising the steps of
   i) inserting a vector comprising recombinant DNA containing the DNA sequence according to claim 1 and plasmid DNA which undergoes autonomous replication in *E. coli* into a microorganism of the species *E. coli* to obtain a transformant,
   ii) cutting the transformant in a suitable medium to produce Leu-DH, and
   iii) separating the Leu-DH from the microorganism.

8. A process for the preparation of non-proteinogenous L-amino acids from the corresponding α-keto acids comprising the step of incubating leucine dehydrogenase prepared according to claim 7 with an α-keto acid.

9. The process according to claim 8 wherein the α-keto acid is selected from the group consisting of 2-oxo-4-methylpentanoic acid, 2-oxo-3-methylpentanoic acid, 2-oxo-3-methylbutanoic acid, 2-oxopentanoic acid, 2-oxo-4-methylhexanoic acid, 2-oxobutanoic acid, 2-oxo-3,3-dimethylbutanoic acid, 2-oxohexanoic acid, 2-oxo-4,4-dimethylpentanoic acid, 2-oxo-3,3-dimethylpentanoic acid, 2-oxo-4-ethylhexanoic acid, 2-oxo-5,5-dimethylhexanoic acid, 2-oxo-3-cyclohexylpropanoic acid and 2-oxo-4,4-dimethylhexanoic acid.

10. The process according to claim 7, wherein said plasmid DNA is DNA from plasmid pUC18.

11. The process according to claim 10, wherein said transformant is the strain *E. coli* XL1-blue pLeu2 deposited under Accession No. DSM 10441.

* * * * *

SEQUENCE LISTING ( 1 ) GENERAL INFORMATION:

( i i i ) NUMBER OF SEQUENCES: 2

( 2 ) INFORMATION FOR SEQ ID NO:1:

( i ) SEQUENCE CHARACTERISTICS:
( A ) LENGTH: 1723 base pairs
( B ) TYPE: nucleic acid
( C ) STRANDEDNESS: double
( D ) TOPOLOGY: linear ( i i ) MOLECULE TYPE: DNA (genomic)

( i i i ) HYPOTHETICAL: NO ( i v ) ANTI-SENSE: NO ( v i ) ORIGINAL SOURCE:
( A ) ORGANISM: Bacillus cereus
( B ) STRAIN: DSM 626

( x i ) SEQUENCE DESCRIPTION: SEQ ID NO:1:

```
CCCGGGCAAT AGGAATCGAC TTGCCAAAAG TGGCACCAAT TGCAGCAGTA GAAGTTGTGA   60
ATCCAGCGAT GCAGGCGACA ATTGATGCAG CGATGTTAAC ACAAATGAAT CGCCGCGGAC  120
AAATTAAAGA TTGTATCGTT GATGGACCAC TTGCTTTAGA TAATGCAGTA TCAACAAATT  180
GCAGCAGAGC ATCAAAGGCA TAGTAAGTGA TGTAGCAGGT AAGGCAGATA TTTTACTCGT  240
CCCAACGATT GAAGCTGGAA ATGTGCTATA TAAATCACTC GTATACTTTG CGGATGCAAA  300
AGTAGGAGCA ATGATTGCTG GCGCAAAAGC ACCGATTGTT TTAACATCTC GTGCTGATTC  360
AGCAGAAACA AAAGTATATT CATTAGCATT GGCAGTTGCG ACTGCTTCAA AATAAACCAA  420
AAAGGGTAAA ACATTAGGGG GAAACGACAA TGACATTAGA AATCTTCGAA TACTTAGAAA  480
AATATGATTA TGAGCAAGTA GTATTTTGTC AAGATAAAGA ATCTGGTTTA AAAGCAATTA  540
TTGCAATTCA TGATACAACA CTTGGACCGG CTCTTGGTGG AACAAGAATG TGGACATATG  600
ATTCTGAAGA AGCGGCGATT GAAGATGCAT TGCGTCTTGC AAAAGGGATG ACATACAAAA  660
ACGCAGCAGC TGGTTTAAAC TTAGGTGGTG CGAAAACAGT AATTATCGGT GATCCTCGTA  720
AAGATAAGAG CGAAGCAATG TTCCGTGCAC TAGGACGTTA TATCCAAGGA CTAAACGGAC  780
GTTACATTAC AGCTGAAGAT GTTGGTACAA CAGTAGATGA TATGGATATT ATCCATGAAG  840
AAACTGACTT TGTAACAGGT ATCTCACCAT CATTCGGTTC TTCTGGTAAC CCATCTCCGG  900
TAACTGCATA CGGTGTTTAC CGTGGTATGA AAGCAGCTGC AAAAGAAGCT TTCGGTACTG  960
ACAATTTAGA AGGAAAAGTA ATTGCTGTTC AAGGCGTTGG TAACGTAGCA TATCACCTAT 1020
GCAAACATTT ACACGCTGAA GGAGCAAAAT TAATTGTTAC AGATATTAAT AAAGAAGCTG 1080
TACAACGTGC TGTAGAAGAA TTCGGTGCAT CAGCAGTTGA ACCAAATGAA ATTTACGGTG 1140
TTGAATGCGA TATTTACGCA CCATGTGCAC TAGGCGCAAC AGTTAATGAT GAAACTATTC 1200
CACAACTTAA AGCAAAAGTA ATCGCAGGTT CTGCGAATAA CCAATTAAAA GAAGATCGTC 1260
ATGGTGACAT CATTCATGAA ATGGGTATTG TATACGCACC AGATTATGTA ATTAATGCAG 1320
GTGGCGTAAT TAACGTAGCA GACGAATTAT ATGGATACAA TAGAGAACGT GCACTAAAAC 1380
GTGTTGAGTC TATTTATGAC ACGATTGCAA AAGTAATCGA AATTTCAAAA CGCGATGGCA 1440
TAGCAACTTA TGTAGCGGCA GATCGTCTAG CTGAAGAGCG CATTGCAAGC TTGAAGAATT 1500
CTCGTAGCAC TTACTTACGC AACGGTCACG ATATTATTAG CCGTCGCTAA TCATTCATAT 1560
```

```
ATAACTTTTA CAAAAGGTGT GGTTACCTCT TATGAGGTTT CCACTTCCTT TTGAATTTAT      1620

TAGTGGAGGT AGCAACATTG TCTGTAAATC GAATTCTTGT TATTAACCCA GGTAGTACAT      1680

CCACAAAAAT TGGTGTTTTT GATAATGAAA GACCCGTTCT AGA                       1723
```

( 2 ) INFORMATION FOR SEQ ID NO:2:

( i ) SEQUENCE CHARACTERISTICS:
        ( A ) LENGTH: 366 amino acids
        ( B ) TYPE: amino acid
        ( D ) TOPOLOGY: linear ( i i ) MOLECULE TYPE: protein ( x i ) SEQUENCE DESCRIPTION: SEQ ID NO:2:

```
Met Thr Leu Glu Ile Phe Glu Tyr Leu Glu Lys Tyr Asp Tyr Glu Gln
 1               5                  10                  15

Val Val Phe Cys Gln Asp Lys Glu Ser Gly Leu Lys Ala Ile Ile Ala
                20                  25                  30

Ile His Asp Thr Thr Leu Gly Pro Ala Leu Gly Gly Thr Arg Met Trp
                35                  40                  45

Thr Tyr Asp Ser Glu Glu Ala Ala Ile Glu Asp Ala Leu Arg Leu Ala
        50                  55                  60

Lys Gly Met Thr Tyr Lys Asn Ala Ala Ala Gly Leu Asn Leu Gly Gly
 65                 70                  75                  80

Ala Lys Thr Val Ile Ile Gly Asp Pro Arg Lys Asp Lys Ser Glu Ala
                85                  90                  95

Met Phe Arg Ala Leu Gly Arg Tyr Ile Gln Gly Leu Asn Gly Arg Tyr
                100                 105                 110

Ile Thr Ala Glu Asp Val Gly Thr Thr Val Asp Asp Met Asp Ile Ile
                115                 120                 125

His Glu Glu Thr Asp Phe Val Thr Gly Ile Ser Pro Ser Phe Gly Ser
        130                 135                 140

Ser Gly Asn Pro Ser Pro Val Thr Ala Tyr Gly Val Tyr Arg Gly Met
145                 150                 155                 160

Lys Ala Ala Ala Lys Glu Ala Phe Gly Thr Asp Asn Leu Glu Gly Lys
                165                 170                 175

Val Ile Ala Val Gln Gly Val Gly Asn Val Ala Tyr His Leu Cys Lys
                180                 185                 190

His Leu His Ala Glu Gly Ala Lys Leu Ile Val Thr Asp Ile Asn Lys
        195                 200                 205

Glu Ala Val Gln Arg Ala Val Glu Glu Phe Gly Ala Ser Ala Val Glu
        210                 215                 220

Pro Asn Glu Ile Tyr Gly Val Glu Cys Asp Ile Tyr Ala Pro Cys Ala
225                 230                 235                 240

Leu Gly Ala Thr Val Asn Asp Glu Thr Ile Pro Gln Leu Lys Ala Lys
                245                 250                 255

Val Ile Ala Gly Ser Ala Asn Asn Gln Leu Lys Glu Asp Arg His Gly
                260                 265                 270

Asp Ile Ile His Glu Met Gly Ile Val Tyr Ala Pro Asp Tyr Val Ile
        275                 280                 285

Asn Ala Gly Gly Val Ile Asn Val Ala Asp Glu Leu Tyr Gly Tyr Asn
        290                 295                 300

Arg Glu Arg Ala Leu Lys Arg Val Glu Ser Ile Tyr Asp Thr Ile Ala
305                 310                 315                 320

Lys Val Ile Glu Ile Ser Lys Arg Asp Gly Ile Ala Thr Tyr Val Ala
                325                 330                 335
```

-continued

```
Ala  Asp  Arg  Leu  Ala  Glu  Glu  Arg  Ile  Ala  Ser  Leu  Lys  Asn  Ser  Arg
               340                      345                     350

Ser  Thr  Tyr  Leu  Arg  Asn  Gly  His  Asp  Ile  Ile  Ser  Arg  Arg
               355                      360                     365
```